(12) United States Patent
Pottage

(10) Patent No.: US 7,741,334 B2
(45) Date of Patent: *Jun. 22, 2010

(54) LOW DOSE THERAPY FOR TREATING VIRAL INFECTIONS

(75) Inventor: John Pottage, Madison, CT (US)

(73) Assignee: Achillion Pharmaceuticals, Inc., New Haven, CT (US)

( * ) Notice: Subject to any disclaimer, the term of this patent is extended or adjusted under 35 U.S.C. 154(b) by 73 days.

This patent is subject to a terminal disclaimer.

(21) Appl. No.: 11/547,179

(22) PCT Filed: Apr. 1, 2005

(86) PCT No.: PCT/US2005/011539

§ 371 (c)(1),
(2), (4) Date: Sep. 29, 2006

(87) PCT Pub. No.: WO2005/097618

PCT Pub. Date: Oct. 20, 2005

(65) Prior Publication Data

US 2007/0208047 A1    Sep. 6, 2007

Related U.S. Application Data

(60) Provisional application No. 60/558,633, filed on Apr. 1, 2004.

(51) Int. Cl.
*A01N 43/54* (2006.01)
*A61K 31/517* (2006.01)
*A01N 43/04* (2006.01)
*A61K 31/70* (2006.01)
*A01N 43/64* (2006.01)
*A61K 31/53* (2006.01)

(52) U.S. Cl. .......................... 514/269; 514/49; 514/243
(58) Field of Classification Search ................ 514/49, 514/243, 269
See application file for complete search history.

(56) References Cited

U.S. PATENT DOCUMENTS 5,703,058 A * 12/1997 Schinazi et al. ................ 514/45
6,908,924 B2   6/2005 Watanabe et al.

FOREIGN PATENT DOCUMENTS

WO    WO 98/57648 A1    12/1998
WO    2000403014 A2    7/2000
WO    2005055955 A2    6/2005
WO    2005097618 A2    10/2005

OTHER PUBLICATIONS

Shi, J., McAtee, J., Wirtz, S.S., Tharnish, P., Juodawlkis, A., Liotta, D.C., and R.F. Schinazi, 1999. Synthesis and biological evaluation of 2',3'-didehydro-2',3'-dideoxy-5-fluorocytidine (D4FC) analogue: Discovery of carbocyclic nucleoside triphosphates with potent inhibitory activity against HIV-1 reverse transcriptase. J. Med. Chem. 42:859-867.*
Chen, Shu-Hui. "Comparative Evaluation of L-Fd4c and Related Nucleotide Analogs as Promising Antiviral Agents," Current Medicinal Chemistry (2002) 9: 899-912.
Dutschman, Ginger E. et al. "Metabolism of 2',3'-Dideoxy-2',3'-Didehydro-Beta-L(−)-5-Flourocytidine and Its Activity in Combination with Clinically Approved Anti-Human Immodeficiency Virus Beta-D(+) Nucleoside Analogs in Vitro," Antimicrobial Agents and Chemotherapy (1998) 42(7): 1799-1804.
Mickle, Travis and Vasu Nair. "Anti-Human Immumodeficiency Virus Activities of Nucleosides and Nucleotides: Correlation with Molecular Electrostatic Potential Data," Antimicrobial Agents and Chemotherapy (2000) 44(11): 2939-2947.
International Search Report for PCT/US05/11538.
Written Opinion of the International Searching Authority for PCT/US05/11539.
International Search Report for PCT/US05/037597, 2005.
Written Opinion for US05/037597, 2005.
Gish, et al., "Dose range study of pharmacokinetic, safety, and preliminary antiviral activity of emtricitabine in adults with hepatitis B virus infection," Antimicrob. Agens Chemother., (2002), 46(6): 1734-1740 (abstract only) .
Johnson, et al., "Clinical Pharmacokinetics of Lannuvudine," Clinical Pharmacokinetic, (1999), 36(1): 41-66 (abstract only).
Patel, J. et al., "ACH-126443 Achillion/Yale University," Current Opinion in Investigation Drugs, (2002), 3(11): 1580-1584.
Sorberra, L.A., et al., "ACH-126443 Anti-HBV, Anti-HIV," Drugs of the Future, (2002), 27(12):1131-1140.
Zoulim, F., et al.,"Animal model for the study of HBV infection and the evaluationof new anti-HBV strategies," Journal of Gastroenterology and Hepatology, (2002), 17: S460-S463.

* cited by examiner

*Primary Examiner*—Sreeni Padmanabhan
*Assistant Examiner*—Samira Jean-Louis
(74) *Attorney, Agent, or Firm*—Cantor Colburn LLP

(57) ABSTRACT

A method of treating viral infections, particularly Hepatitis B (HBV) and Human Immunodeficiency Virus (HIV), by administering a low dose of Elvucitabine to a patient suffering viral infection is provided herein. The Elvucitabine dosages provided herein for effective anti-viral therapy are approximately 10-fold less than the effective dosages of currently marketed reverse transcriptase inhibitors. The Elvucitabine dosage may be given BID, daily, once every 48 hours, or once weekly. Also provided herein are packaged pharmaceutical formulations comprising Elvucitabine and instructions for treating a viral infection by administering a low BID, daily, once/48 hour, or weekly dosage of Elvucitabine. The low dose Elvucitabine formulations provided herein have the additional benefit of improving patient compliance with antiviral therapy.

11 Claims, 10 Drawing Sheets

LOW DOSE THERAPY FOR TREATING VIRAL INFECTIONS

CROSS REFERENCE TO RELATED APPLICATIONS

This application claims priority to U.S. provisional patent application No. 60/558,633, filed Apr. 1, 2004, which is hereby incorporated by reference in its entirety.

FIELD OF THE INVENTION

A method of treating viral infections, particularly Hepatitis B (HBV) and Human Immunodeficiency Virus (HIV), by administering a low dose of Elvucitabine to a patient suffering viral infection is provided herein. The Elvucitabine dosage may be given BID, daily, once ever 48 hours, or once weekly. Also provided herein are packaged pharmaceutical formulations comprising Elvucitabine and instructions for treating a viral infection by administering a low BID, daily, once/48 hour, or weekly dosage of Elvucitabine. Methods of improving patient compliance with anti-viral therapy by providing a reverse transcriptase inhibitor formulated for low dose administration are also included herein.

The invention provides novel pharmaceutical formulations of Elvucitabine. The invention also provides pharmaceutical compositions and oral dosage forms having unique physical—chemical properties.

BACKGROUND

Hepatitis B virus (HBV) infection is a major health problem throughout the world. HBV is a causative agent of both an acute and chronic form of hepatitis. It is estimated that more than 200 million people worldwide are chronic carriers of HBV.

HBV belongs to the family Hepadnaviridae, which includes a number of related viruses that primarily infect small rodents. All members of the hepadnavirus family have a number of characteristics in common such as morphological appearance, antigenic makeup and DNA size and structure. Pathological findings following infection with the members of this family are quite similar. Studies show that the replication and spread of the viruses of this family are dependent upon the reverse transcriptase of an RNA intermediate.

HBV is a double-stranded DNA virus. Its DNA polymerase catalyzes both DNA-dependent and RNA-dependent RNA synthesis. The life cycle of HBV involves the enzyme reverse transcriptase in its DNA replication.

Although acute HBV infections are generally self-limiting, in many instances the disease can progress to the chronic state. HBV infection also creates a risk to fulminant hepatitis. In addition, Hepatitis B viral infections are closely associated with hepatocellular carcinoma.

AIDS is a generally fatal disease caused by a human pathogenic retrovirus known as human immunodeficiency virus (HIV), which includes HIV-1 and HIV-2. Reverse transcriptase plays an essential role in the elaboration and life cycle of HIV and consequently, the progress of the disease. Reverse transcriptase inhibitors are currently used with other classes of anti-viral agents to slow and in some cases halt the progress of HIV infection.

Reverse transcriptase inhibitors are preferred therapeutics for treating certain viral infections, particularly HBV and HIV infections. Typically about 300 mg of a reverse transciptase inhibitor must be administered daily for effective treatment of a viral infections, sometimes on a once per day dosing schedule, but more typically on a twice or three times per day dosing schedule. Because patients suffering from HBV or HIV often take a number of medications, a reverse transcriptase inhibitor efficacious at lower dosages is urgently needed. A reverse transcriptase inhibitor that can be administered once daily or less frequently is particularly desireable.

Elvucitabine is a nucleoside analog of the formula

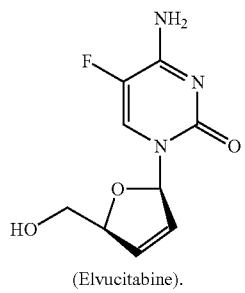

(Elvucitabine).

The anti-viral properties of Elvucitabine have been described previously in U.S. Pat. Nos. 5,621,120, 5,627,160, and 5,839,881, and U.S. patent application Ser. No. 10/411,929, filed Apr. 11, 2004, which are hereby incorporated by reference for their teachings regarding the use of Elvucitabine for treating viral infections, including HBV and HIV infections, and for teachings regarding the chemical synthesis of Elvucitabine.

SUMMARY OF THE INVENTION

It has been discovered that Elvucitabine, a reverse transcriptase inhibitor, is efficacious for treating viral infections when administered at very low dosages. Furthermore it has been discovered that this compound is an effective anti-viral agent when administered as infrequently as one time per week.

Elvucitabine, a reverse transcriptase inhibitor, is efficacious for treating viral infections, including HIV infections, when administered at very low dosages. Furthermore, Elvucitabine is an effective anti-viral agent (including anti-HIV efficacy) when as little as about 2.5 mg to about 10 mg is administered once a day. For some patients, including patients having an HIV or HBV infection, Elvucitabine may be effective when administered as infrequently as one time per week. Thus, methods of treating viral infections, including HIV and HBV infections, comprising administering about 2.5 mg to about 10 mg Elvucitabine per day, or about 5 mg to about 20 mg Elvucitabine per 48 hour interval, or about 40 mg to about 100 mg Elvucitabine per week to a patient having a viral infection, such as an HIV or HBV infection.

Methods of administering the Elvucitabine as an oral dosage form are preferred.

Pharmaceutical compositions containing about 2.5 mg to about 10 mg Elvucitabine and suitable for once per day administration, or containing about 5 mg to about 20 mg Elvucitabine and suitable for administration once per 48 hour interval, or about 40 mg to about 100 mg Elvucitabine and suitable for once per week administration, are provided herein.

Packaged pharmaceutical formulations comprising an Elvucitabine pharmaceutical formulation and instructions for using the formulation for treating a viral infection by administering about 2.5 mg to about 10 mg Elvucitabine per day, about 5 mg to about 20 mg Elvucitabine per 48 hour interval, or about 40 mg to about 100 mg Elvucitabine per week, to a patient suffering from a viral infection, such as an HIV or HBV infection, are provided herein.

Also provided herein are methods of increasing patient compliance with anti-viral therapy, such as treatment of an HIV or HBV infection, by providing a reverse transcriptase inhibitor formulated for low dose daily administration, administration once every 48 hour interval, or once weekly administration. Elvucitibane is the preferred reverse transcriptase inhibitor used in such formulations.

DETAILED DESCRIPTION OF THE INVENTION

Terminology

Figure 1:
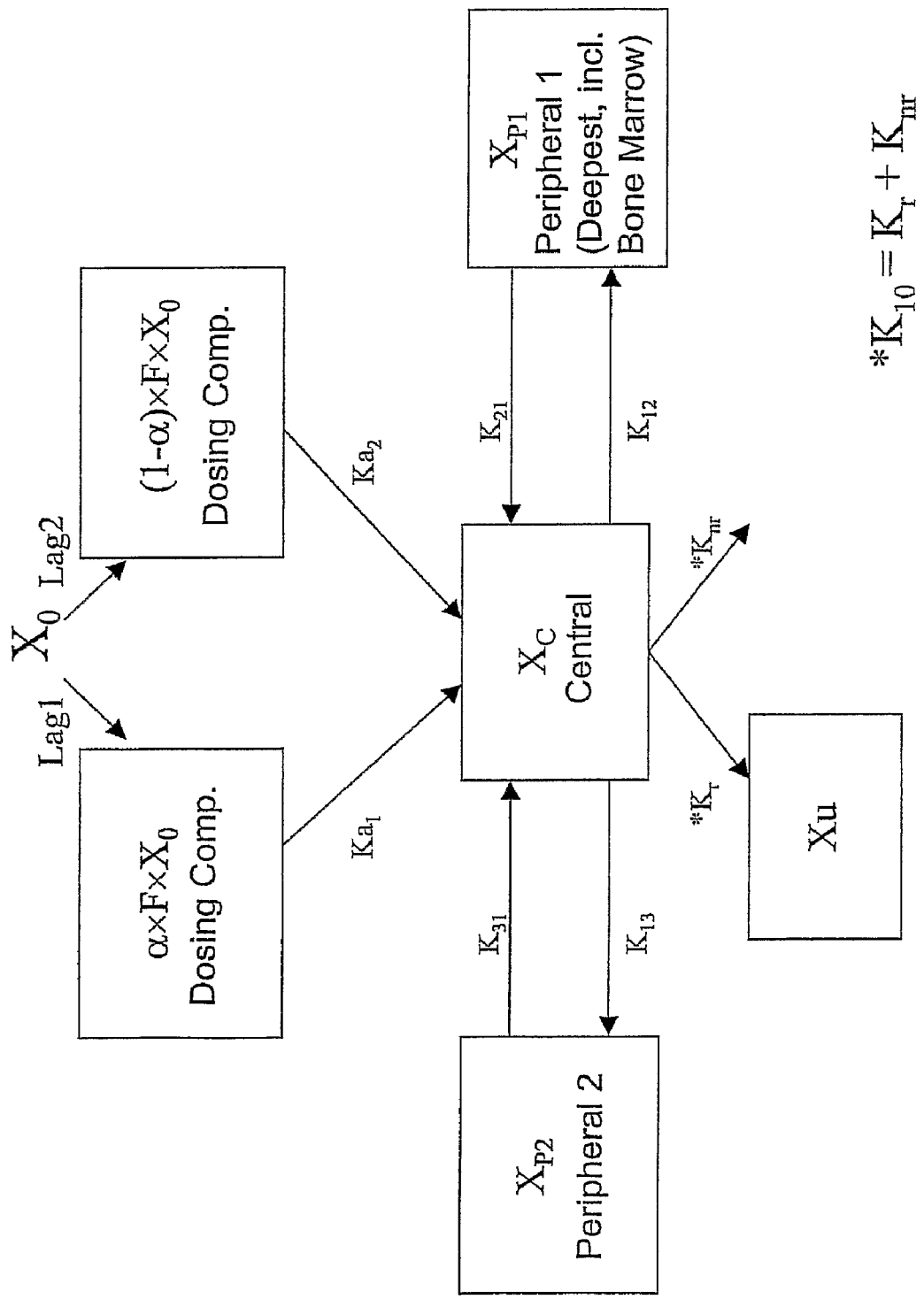
FIG. 1 illustrates a PK model of Elvucitabine.

Prior to setting forth the invention in detail, it may be helpful to provide definitions of certain terms to be used herein. Compounds of the present invention are described using standard nomenclature. Unless defined otherwise, all technical and scientific terms used herein have the same meaning as is commonly understood by one of skill in the art to which this invention belongs.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising", "having", "including", and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. "About" indicates an approximate amount, including the quantity it modifies. When "about" is used to modify a quantity of Elvucitabine, the free, unsalted form is the type of form of elvucitabine referred to, unless another elvucitabine form is expressly stated. No language in the specification should be construed as indicating any non-claimed element as essential to the practice of the invention.

The term "Elvucitabine" is meant to include solvates (including hydrates) of the free compound or salt, crystalline and non-crystalline forms, isotopically enriched or labeled forms, as well as various polymorphs of Elvucitibane, i.e. 4-amino-5-fluoro-1-((2R5S)-5-(hydroxymethyl)-2,5-dihydrofuran-2-yl)pyrimidin-2(1H)-one.

Elvucitabine, contains asymmetric elements and can exist in different stereoisomeric forms. Elvucitabine can be, for example, a racemate or optically active form. While the 4-amino-5-fluoro-1-((2R,5S)-5-(hydroxymethyl)-2,5-dihydrofuran-2-yl)pyrimidin-2(1H)-one is preferred, methods of using racemic mixtures of Elvucitabine, and other optically pure stereoisomers of this compounds are withing the scope of this invention. "Elvucitabine" particularly includes pharmaceutically acceptable salts of this compound.

Isotopes include those atoms having the same atomic number but different mass numbers. By way of general example, and without limitation, isotopes of hydrogen include tritium and deuterium and isotopes of carbon include $^{11}C$, $^{13}C$, and $^{14}C$.

In some embodiments the second active agent is a "low dose active agent." Within the art of HIV treatment certain compounds that enhance the activity of antiviral agents by inhibiting liver enzymes that breakdown antiviral agents are sometimes referred to as "low dose active agents". Ritonovir (NORVIR, Abbot Laboratories, Abbott Park, Ill.) is an example of such a compound. While low dosages of Elvucitabine may be administered with ritonovir, the term "low dose active agent" is used herein to describe compounds that retain therapeutic efficacy when administered in small amounts, typically about 2.5 mg to about 10 mg daily, about 5 to about 20 mg every 48 hours, or about 40 to about 100 mg once weekly, or on another infrequent dosage schedule, typically once daily or less frequently.

"Pharmaceutically acceptable salts" includes derivatives of the disclosed compounds, wherein the parent compound is modified by making non-toxic acid or base addition salts thereof, and further refers to pharmaceutically acceptable solvates, including hydrates, of such compounds and such salts. Examples of pharmaceutically acceptable salts include, but are not limited to, mineral or organic acid addition salts of basic residues such as amines; alkali or organic addition salts of acidic residues such as carboxylic acids; and the like, and combinations comprising one or more of the foregoing salts. The pharmaceutically acceptable salts include non-toxic salts and the quaternary ammonium salts of the parent compound formed, for example, from non-toxic inorganic or organic acids. For example, non-toxic acid salts include those derived from inorganic acids such as hydrochloric, hydrobromic, sulfuric, sulfamic, phosphoric, nitric and the like; other acceptable inorganic salts include metal salts such as sodium salt, potassium salt, cesium salt, and the like; and alkaline earth metal salts, such as calcium salt, magnesium salt, and the like, and combinations comprising one or more of the foregoing salts.

Pharmaceutically acceptable organic salts include salts prepared from organic acids such as acetic, trifluoroacetic, propionic, succinic, glycolic, stearic, lacetic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_n$—COOH where n is 0-4, and the like; organic amine salts such as triethylamine salt, pyridine salt, picoline salt, ethanolamine salt, triethanolamine salt, dicyclohexylamine salt, N,N'-dibenzylethylenediamine salt, and the like; and amino acid salts such as arginate, asparginate, glutamate, and the like, and combinations comprising one or more of the foregoing salts.

"BID administration" is twice daily administration of a compound. Typically, each day two equal dosages of a therapeutic compound are given during waking hours. "TID administration" is administration of a therapeutic compound three times daily. Typically three equal dosages are given each day during waking hours. Some compounds administered BID or TID equal dosages are given with food, several hours apart, during waking hours.

The term "effective amount" means an amount effective, when administered to a human or non-human patient, to provide a therapeutic benefit such as an amelioration of symptoms, e.g., an amount effective to decrease the symptoms of a viral infection, and preferably an amount sufficient to reduce the symptoms of an HBV or HIV infection. In certain circumstances a patient suffering from a viral infection may not present symptoms of being infected. Thus a therapeutically effective amount of a compound is also an amount sufficient to prevent a significant increase or significantly reduce the detectable level of virus or viral antibodies in the patient's blood, serum, or tissues. A significant increase or reduction in the detectable level of virus or viral antibodies is any detectable change that is statistically significant in a standard parametric test of statistical significance such as Student's T-test, where $p<0.05$.

The term "dosage form" denotes a form of a formulation that contains an amount sufficient to achieve a therapeutic effect with a single administration.

The term "oral dosage form" is meant to include a unit dosage form prescribed or intended for oral administration. An oral dosage form may or may not comprise a plurality of subunits such as, for example, microcapsules or microtablets, packaged for administration in a single dose.

"Pharmacokinetic parameters," (PK) are parameters, which describe the in vivo characteristics of Elvucitabine over time, including for example the in vivo dissolution characteristics and plasma concentration of mecaymylamine or other active agent. By "$C_{max}$" is meant the measured concentration of Elvucitabine in the plasma at the highest observed concentration. By "$C_{24}$" is meant the concentration of Elvucitabine in the plasma at about 24 hours. The term "$T_{max}$" refers to the time at which the concentration of Elvucitabine in the plasma is the highest. "AUC" is the area under the curve of a graph of the concentration of Elvucitabine (typically plasma concentration) vs. time, measured from one time to another.

By "subunit" is meant to include a composition, mixture, particle, etc., that can provide an oral dosage form alone or when combined with other subunits. By "part of the same subunit" is meant to refer to a subunit comprising certain ingredients. For example, a subunit comprising Elvucitabine or other active agent and an additional active ingredient may be placed together with additional subunits in a capsule to provide an oral dosage form.

Pharmacokinetics and Pharmacodynamics Modeling to Optimize the Therapeutic Index of Elvucitabine Pharmacokinetics and pharmacodynamics modeling was used to explore potential dosing regimens for Elvucitabine. A pharmacokinetics (PK) model was developed to describe both the plasma concentration-time data and excreted urinary amounts from previously completed studies with Elvucitabine. With the PK model in hand and pharmacodynamics (PD) results of previously completed studies, the relationship of PK and PD from an efficacy and toxicity standpoint is obtained. From the results of the PK and PD studies, a therapeutic window of Elvucitabine is defined and simulated dosing regimens ranging from 5 mg BID to 100 mg Q1 week were explored using ADAPT II® Pharmacokinetic and Pharmacodynamic Systems Analysis Software. From the simulated dosing regimen results, ten dosing regimens were identified allowing maintenance therapy with Elvucitabine at levels effective against both HIV and HBV while avoiding bone toxicity.

Pharmacokinetics:

The PK model created included an individual compartmental PK analysis using ADAPT-II® and Population PK analysis using an iterative two-stage population modeling technique (IT2S®) of plasma and urine data from a study of healthy subjects, n=29, 1×20 mg tablet PO ($ACH_{443}$-011). FIG. 1 illustrates the PK model of Elvucitabine according to a three compartment model characterized by two absorption peaks, each associated with a lag time and a first order absorption rate constant.

Figure 2:
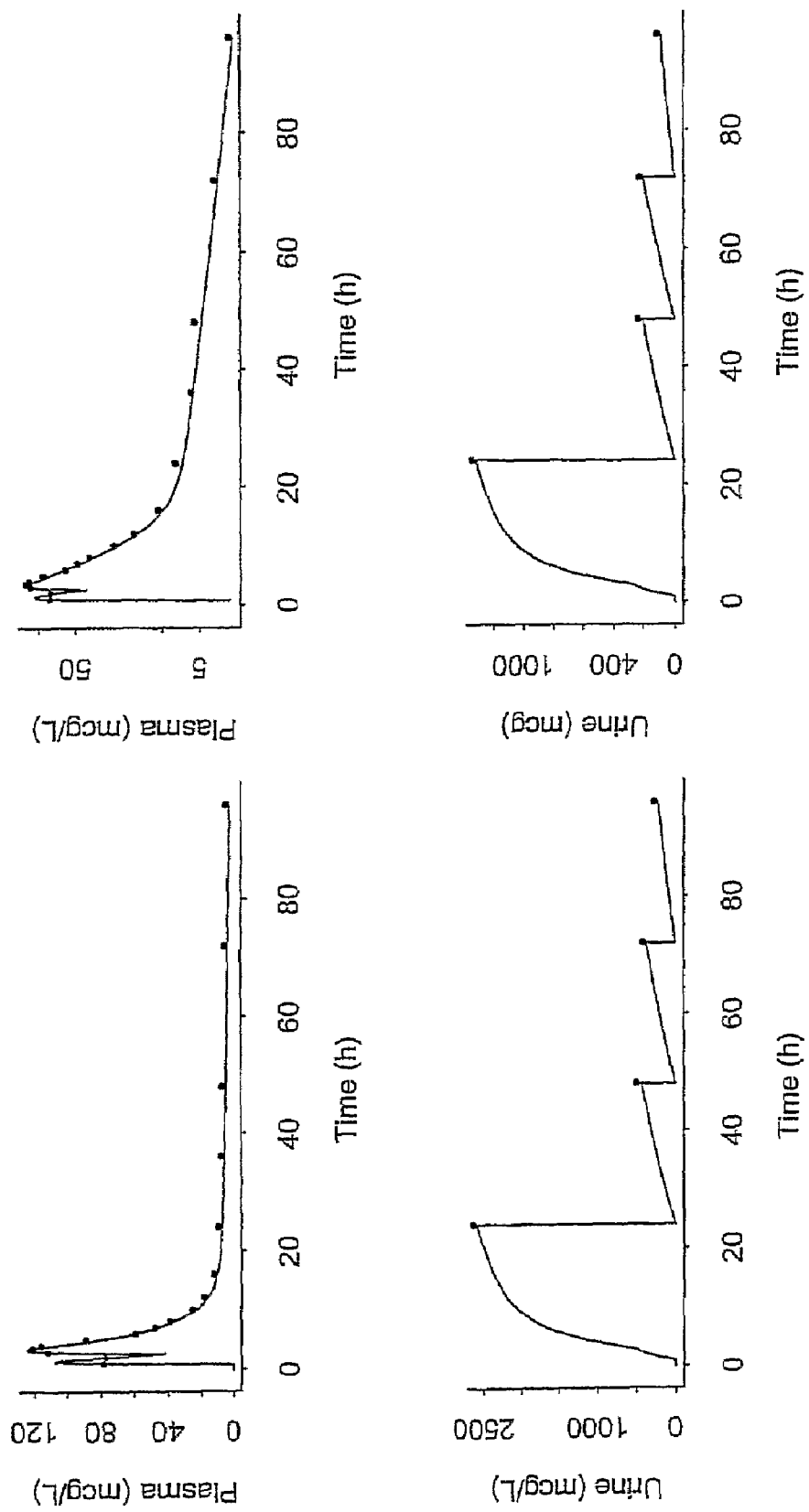
FIG. 2 illustrates an example of individual fit using Pop PK analysis (IT2S)

The Population PK parameters of Elvucitabine include a large apparent volume of distribution ($V_{SS}$) of 1600 L; an early distribution ($\lambda_1$) half-life of 0.59 hour, followed by another distribution ($\lambda_2$) half-life of 30 hours; and an elimination ($\lambda_2$) half-life of 175 hours. Additional parameters include an oral clearance (CL/F) of 16 L/h and the fraction of drug excreted unchanged in urine was about 40%. Table 1 provides the Population PK parameters of Elvucitabine. FIG. 2 illustrates an example of individual fit using a Population PK analysis (IT2S).

TABLE 1

Population PK Parameters of Elvucitabine:

| | | | |
|---|---|---|---|
| Alpha | 0.338 | | |
| Tlag1 | 1.46 h | Ka1 | 1.1 l/h |
| Tlag2 | 2.76 h | Ka2 | 0.292 l/h |
| Vss/F | 1632 L | Vc/F | 30.6 L |
| | | Vp1/F | 1232 L |
| | | Vp2/F | 369 L |
| CL/F | 15.8 L/h | CLnr/F | 9.51 L/h |
| Fu | 39.6% | CLr | 6.29 L/h |
| $T_{half1}$ | 0.586 h | K10 | 0.515 l/h |
| $T_{half2}$ | 30.5 h | K12 | 0.246 l/h |
| $T_{half3}$ | 175 h | K13 | 0.409 l/h |
| | | K21 | 0.006 l/h |
| | | K31 | 0.034 l/h |

Figure 3:
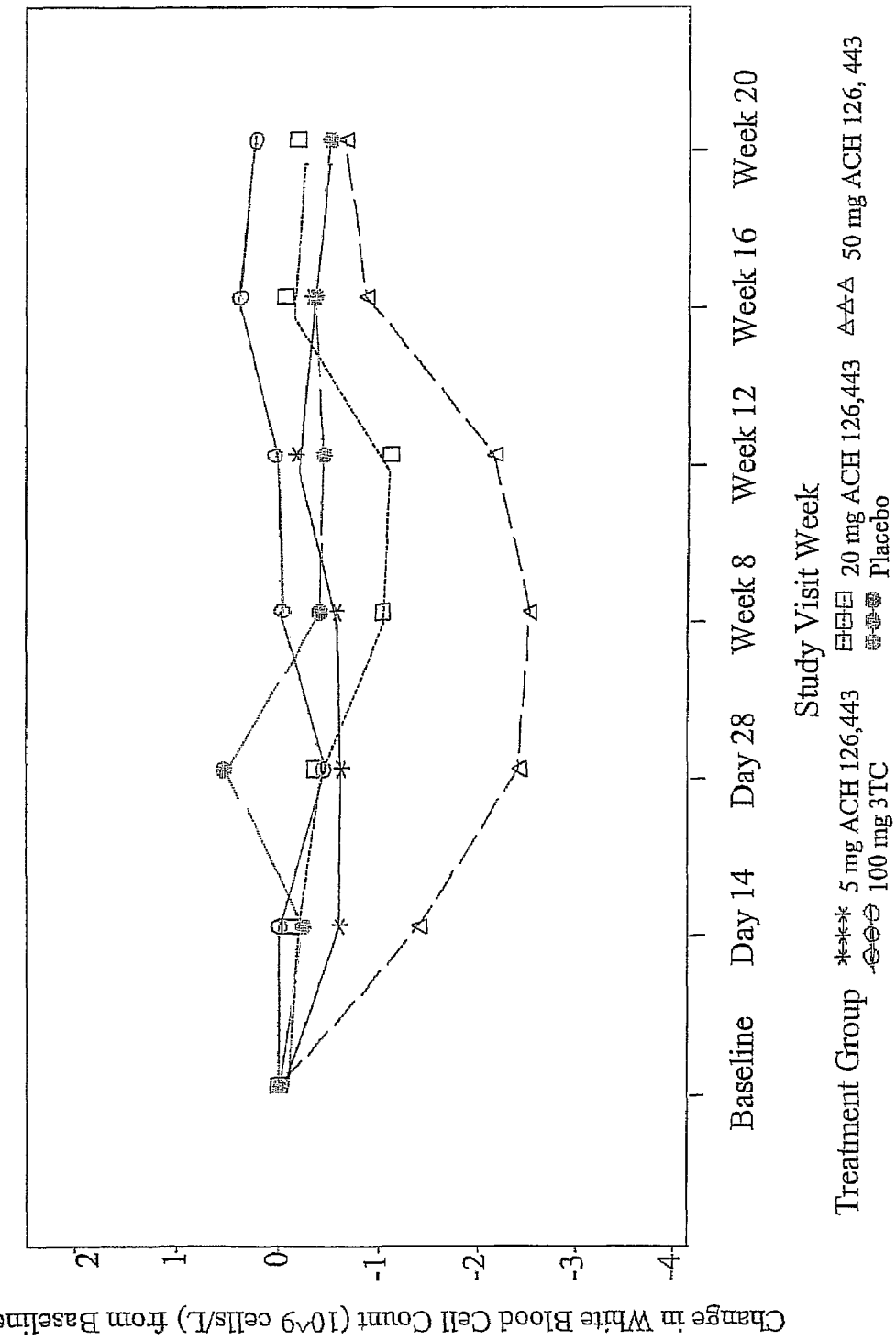
FIG. 3 illustrates the change in mean white blood cell count from baseline for 5 mg, 20 mg, and 50 mg Elvucitabine PD study over 20 weeks.
Figure 4:
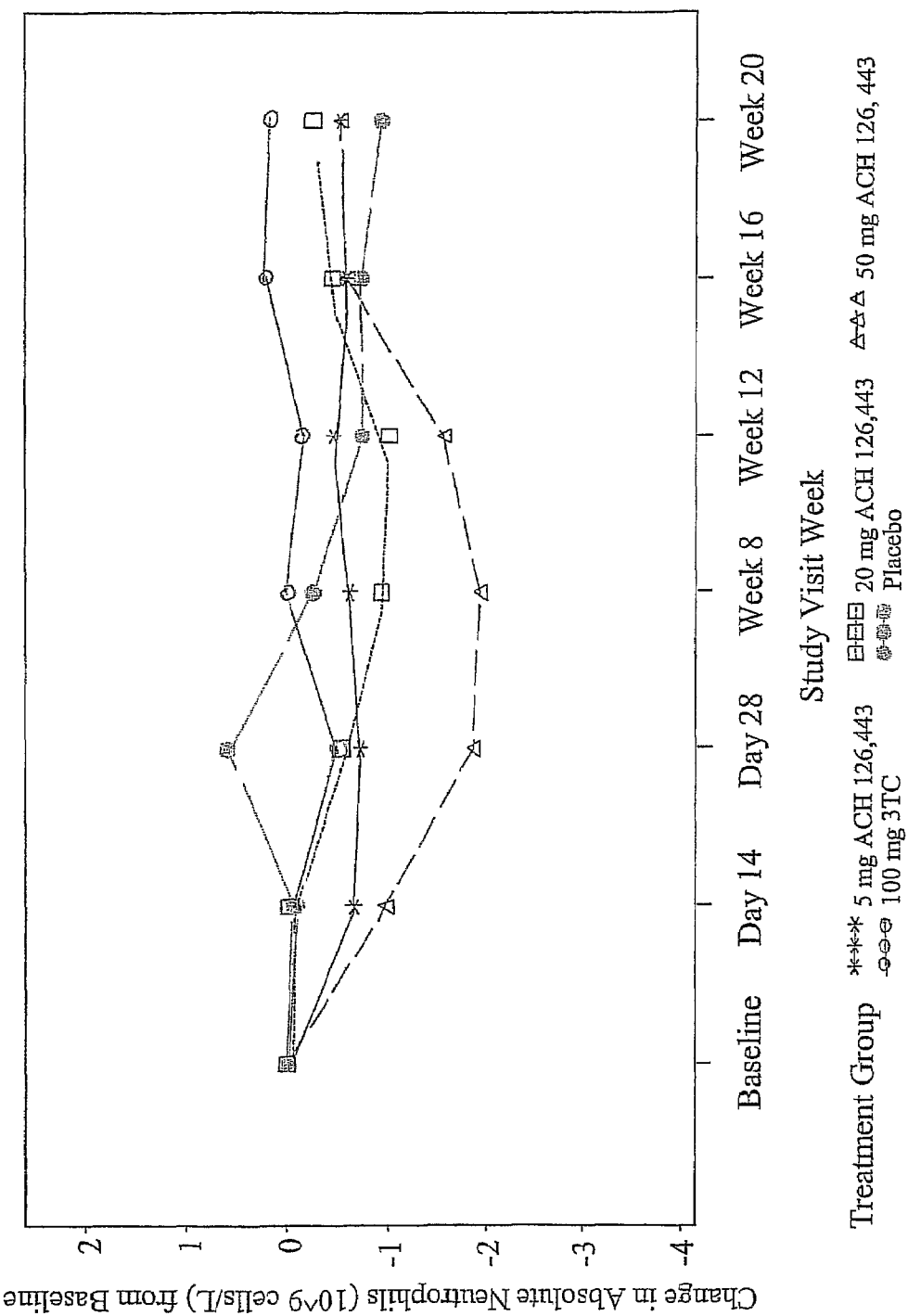
FIG. 4 illustrates the change in mean absolute neutrophils from baseline for 5 mg, 20 mg, and 50 mg Elvucitabine PD study over 20 weeks.

Pharmacodynamics:

Pharmacodynamics of Elvucitabine was explored by analysis of hematology (absolute neutrophil count, ANC) data obtained from a 12 week study in HBV patients. FIG. 3 illustrates the change in mean white blood cell count from baseline for three dosages of Elvucitabine (5 mg, 20 mg, and 50 mg), 100 mg 3TC, and placebo. Only the highest dose of Elvucitabine (50 mg) showed a significant decrease in white blood cell count. FIG. 4 is a graphic representation of the change in absolute neutrophils from baseline for the same study. Table 2 provides absolute neutrophil count at $10^9$/L for the three doses resulting in a baseline estimated as the mean ANC of about $4\times10^9$/L. A 25 percent decrease in the mean ANC corresponds to about $3\times10^9$/L, the threshold for the start of toxicity.

TABLE 2

PD data: Absolute Neutrophil Count ($10^9$/L)

| Study Treatment | Week 0 | Week 2 | Week 4 | Week 8 | Week 12 |
|---|---|---|---|---|---|
| 5 mg PO daily (n = 17) | | | | | |
| Mean | 4.1 | 3.4 | 3.4 | 3.5 | 3.6 |
| (Range) | (1.6-6.9) | (1.5-6.8) | (1.4-6.4) | (1.1-5.9) | (1.7-5.2) |
| 20 mg PO daily (n = 20) | | | | | |
| Mean | 3.8 | 3.7 | 3.2 | 2.8 | 2.7 |
| (Range) | (1.8-6.2) | (2.1-9.0) | (1.0-6.8) | (1.1-4.8) | (1.2-4.8) |
| 50 mg PO daily (n = 19) | | | | | |
| Mean | 4.1 | 3.1 | 2.3 | 2.2 | 2.6 |
| (Range) | (1.7-7.7) | (1.5-8.2) | (0.9-5.6) | (0.8-5.7) | (1.0-5.7) |
| Placebo (n = 8) | | | | | |
| Mean | 4.3 | 4.3 | 4.9 | 4.1 | 3.6 |
| (Range) | (1.8-8.4) | (1.7-9.6) | (1.8-10.7) | (2.1-8.8) | (2.4-6.4) |

Figure 5:
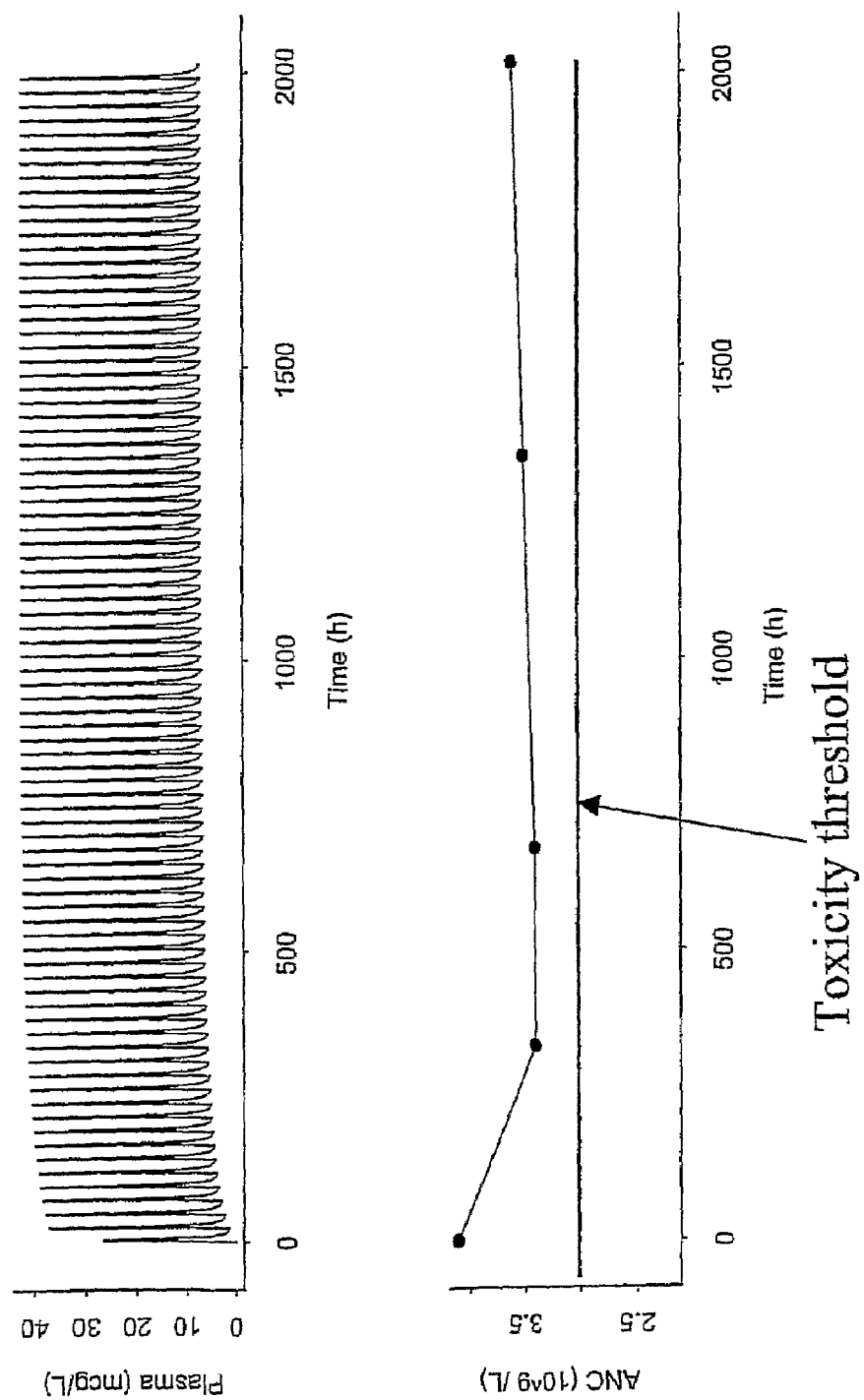
FIG. 5 illustrates simulated plasma concentrations and mean observed ANC for 5 mg QD dose.
Figure 6:
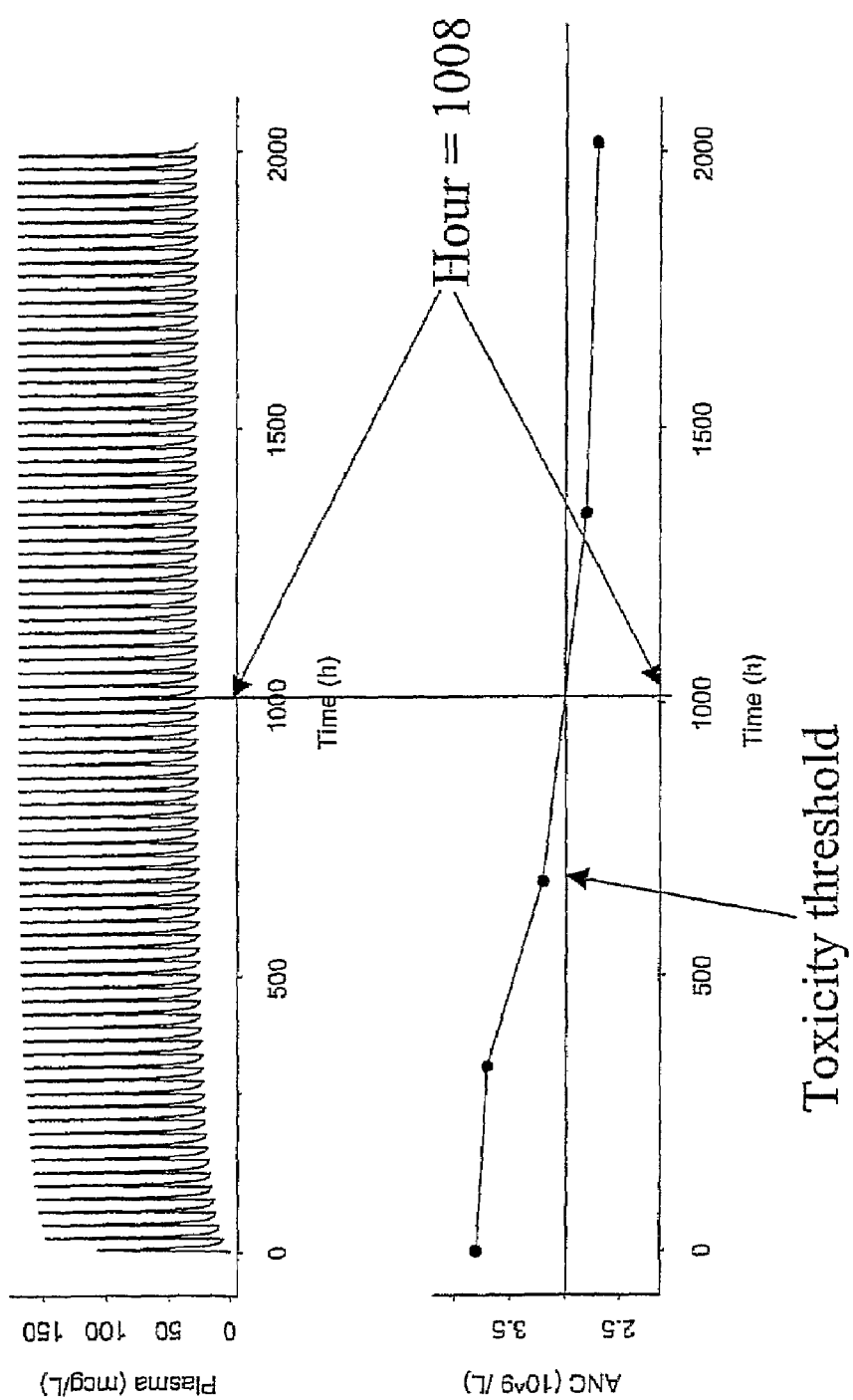
FIG. 6 illustrates simulated plasma concentrations and mean observed ANC for 20 mg QD dose.
Figure 7:
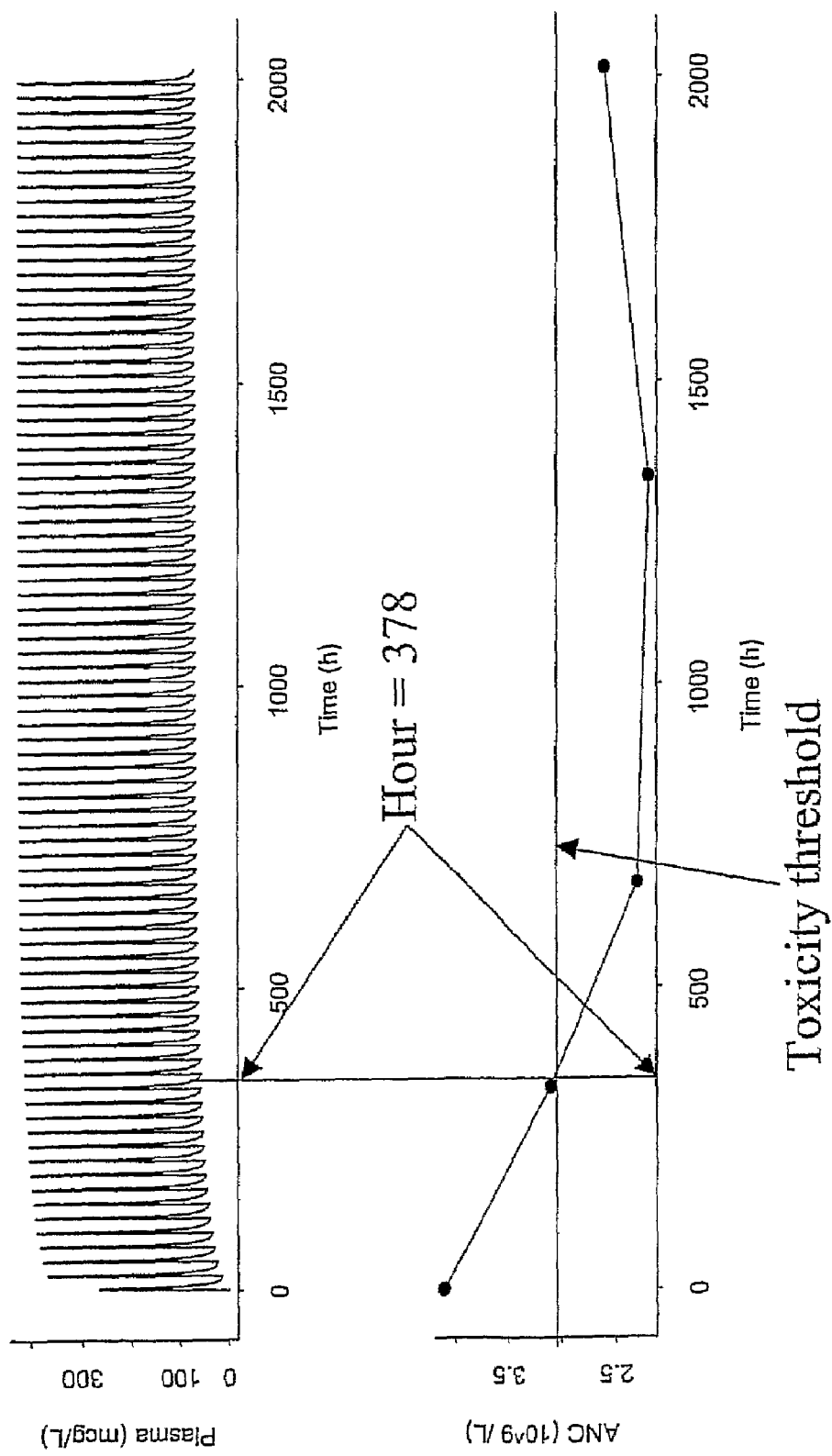
FIG. 7 illustrates simulated plasma concentrations and mean observed ANC for 50 mg QD dose.

FIG. 5 provides a plot of the mean observed ANC and a simulated concentration-time profile for the 5 mg QD dose. As shown by the graph, the toxicity threshold is not met by the dosing regimen. As provided in FIG. 6, the 20 mg QD dose crosses the toxicity threshold at about 1008 hours. Increasing the dose to 50 mg QD results in reaching the toxicity threshold at 378 hours (FIG. 7).

Figure 8:
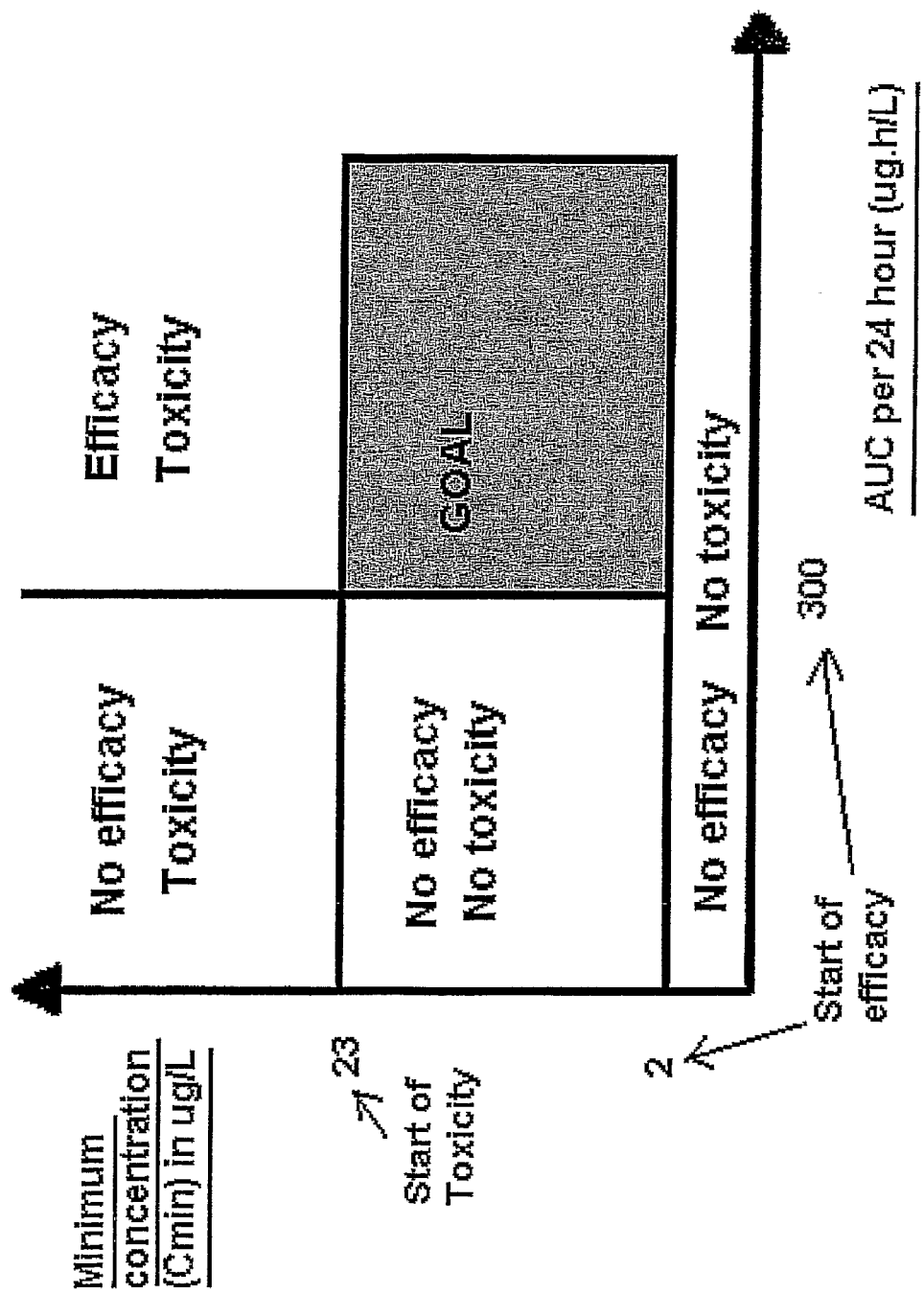
FIG. 8 is a schematic of the relationship of PK versus PD for Elvucitabine.

From the foregoing results, a therapeutic window of Elvucitabine was identified. It has been determined that a 5 mg QD dose is effective for HBV and, therefore, a plasma AUCss/24 of 300 μg·h/L was identified as the efficacy threshold. Furthermore, as Elvucitabine exhibits an in vitro $IC_{50}$ for HIV of 4.8 nM, which corresponds to 1.08 μg/L, the $C_{min}$ for efficacy was determined to be ≧2 μg/L. The onset of toxicity (ANC<$3 \times 10^9$/L) linked to the deepest (P1) compartment is $C_{max}$>40 μg/L, which correlates to a central compartment (plasma) $C_{min}$≧23 μg/L. A conservative therapeutic window is determined to have an AUCss/24>300 μg·h/L; $C_{min}$ Central≧2 μg/L, but<23 μg/L; and a $C_{max}$ P1<40 μg/L. FIG. 8 provides a schematic of the relationship of PK versus PD where the targeted $C_{min}$ and AUC/24 that provides efficacy without toxicity is desired.

Figure 9:
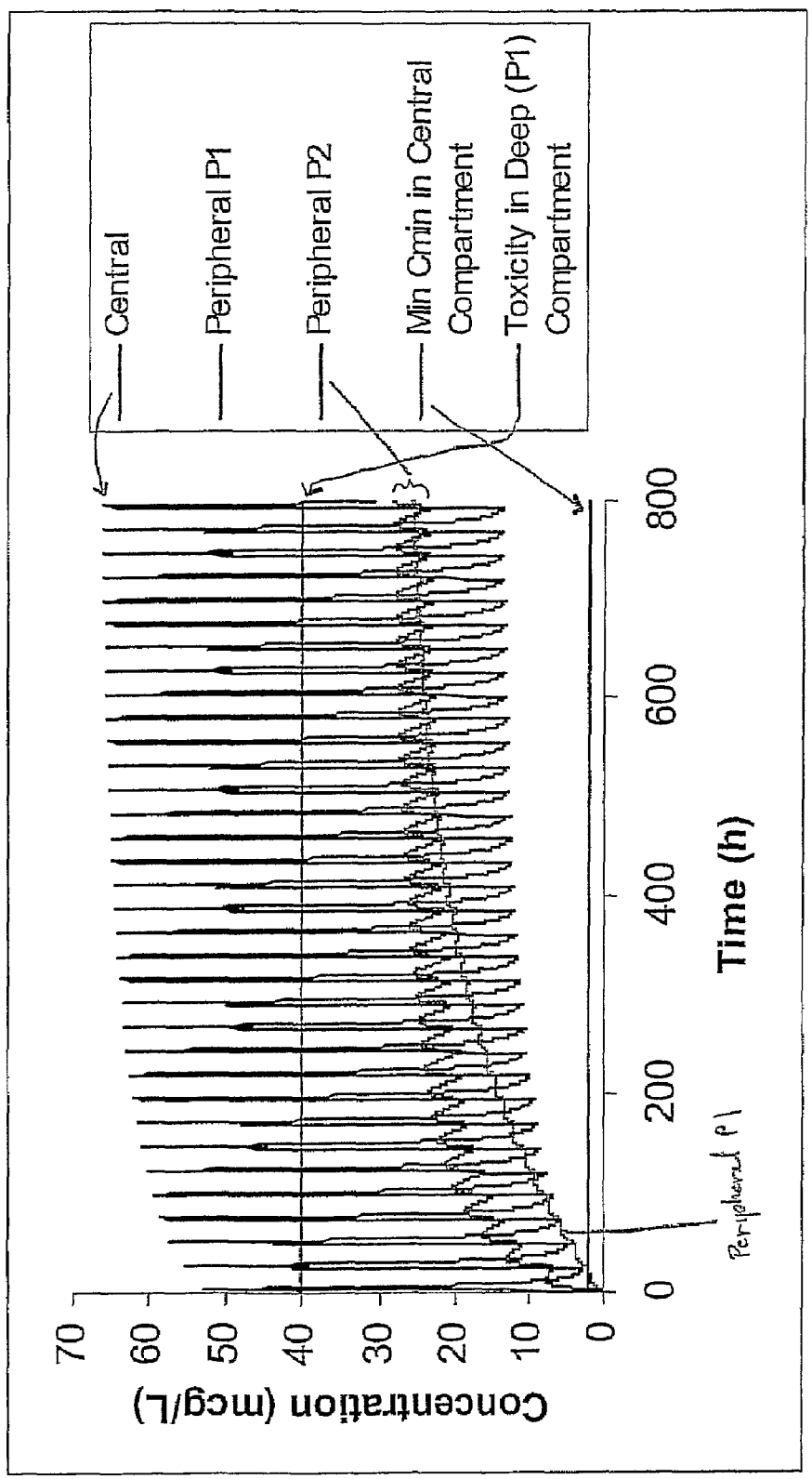
FIG. 9 is an example of a simulated dosing regimen of a 10 mg QD.
Figure 10:
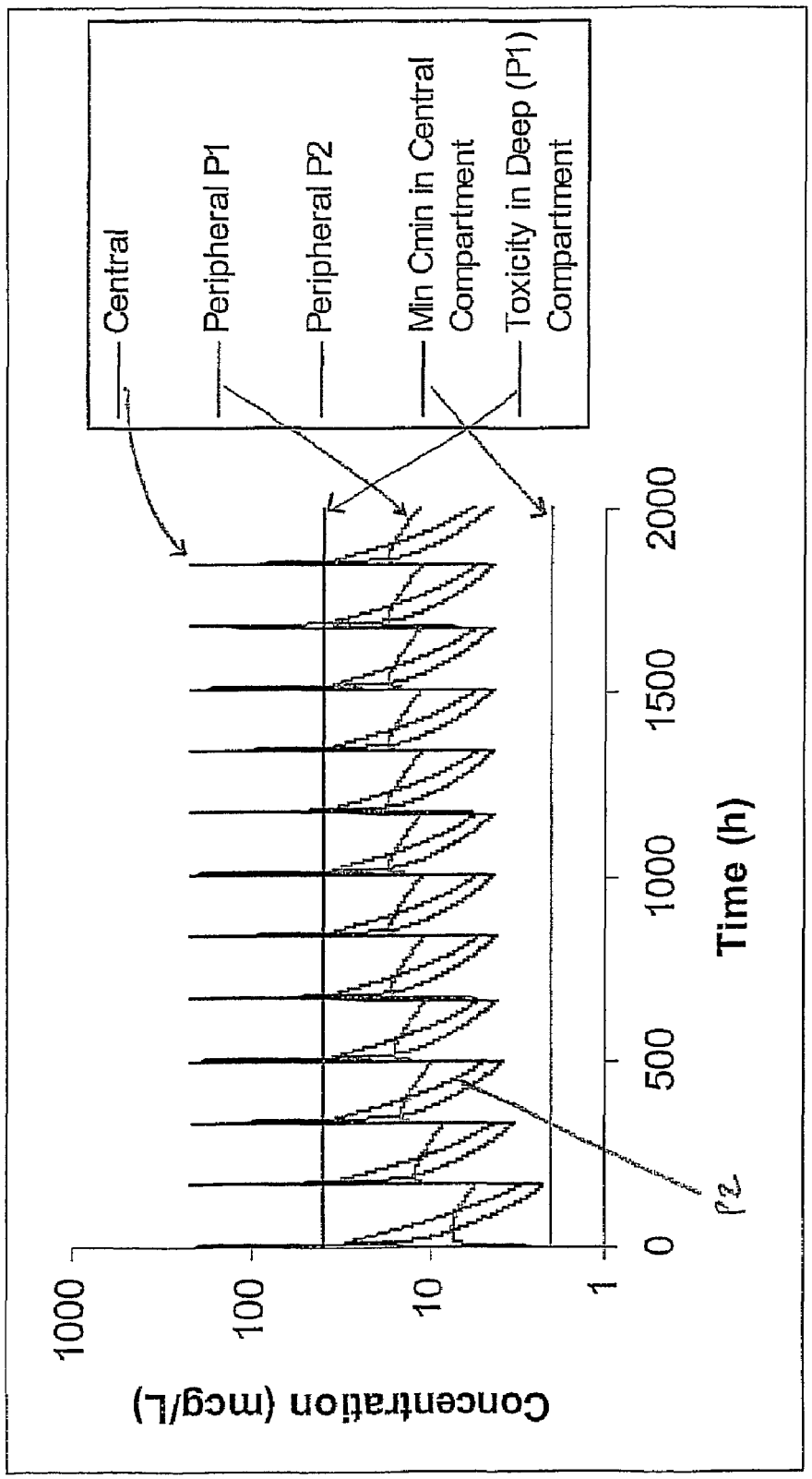
FIG. 10 is an example of a simulated dosing regimen of a 40 mg Q1 week.

From the PK and PD analyses, twenty-nine dosing regimens were simulated using ADAPT II®. The dosing regimens simulated ranged from 5 mg twice a day to 100 mg Q1week and are provided in Table 3. An asterisk (*) indicates those results outside of the defined therapeutic window. From the study, ten dosing regimens were identified that meet the therapeutic window: one twice a day regimen at 5 mg; three once a day regimens at 5 mg, 7.5 mg, and 10 mg; three once every 48 hour regimens at 10 mg, 15 mg, and 20 mg; and three once a week regimens at 30 mg, 40 mg, and 50 mg. Surprisingly, three regimens with a once weekly dosing have been identified that would allow maintenance therapy with Elvucitabine at levels effective against both HIV and HBV while avoiding bone marrow toxicity. FIG. 9 provides a simulated concentration-time profile of 10 mg QD dosing regimen while FIG. 10 provides a profile for 40 mg Q1 week dosing. The 40 mg Q1 week dosing regimen, according to the model, provides the desired efficacy while at the same time avoiding the toxicity threshold.

TABLE 3

Elvucitabine Dosing Regimens:

| Schedule | Parameters | 5 mg | 7.5 mg | 10 mg | 15 mg | 20 mg | 30 mg | 40 mg | 50 mg | 75 mg | 100 mg |
|---|---|---|---|---|---|---|---|---|---|---|---|
| BID Sim. end 2016 hr (336 doses) | AUCtau Central/ 24 hr | 634.1 | 951.1 | 1268 | 1902 | 2536 | | | 6341 | | |
| | Cmin Central (last tau) | 16.2 | 24.3* | 32.4* | 48.6* | 64.8* | — | — | 162* | — | — |
| | Cmax P1 | 26.6 | 39.8 | 53.1* | 79.7* | 106* | | | 266* | | |
| QD Sim. end 2016 hr (168 doses) | AUCtau Central/ 24 hr | 317 | 476 | 634 | 951 | 1269 | | | 3172 | | |
| | Cmin Central (last tau) | 6.94 | 10.4 | 13.9 | 20.8 | 27.8* | — | — | 69.4* | — | — |
| | Cmax P1 | 13.4 | 20.1 | 26.8 | 40.2* | 53.6* | | | 134* | | |
| Q48H Sim. end 2016 hr (84 doses) | AUCtau Central/ 24 hr | 159* | 238* | 317 | 476 | 634 | | | 1586 | 2378 | 3171 |
| | Cmin Central (last tau) | 3.05 | 4.58 | 6.11 | 9.16 | 12.2 | — | — | 30.5* | 45.8* | 61.1* |
| | Cmax P1 | 6.87 | 10.3 | 13.7 | 20.6 | 27.5 | | | 68.7* | 103* | 137* |
| Q1week Sim end 5376 hr (32 doses) | AUCtau Central/ 24 hr | | 67.7* | 90.3* | 135* | 181* | 271* | 361 | 451 | 677 | 903 |
| | Cmin Central (last tau) | — | 0.811* | 1.08* | 1.62* | 2.16 | 3.24 | 4.32 | 5.40 | 8.11 | 10.8 |
| | Cmax P1 | | 3.36 | 4.48 | 6.72 | 8.96 | 13.4 | 17.9 | 22.4 | 33.6 | 44.8* |

*Results are outside of therapeutic window

Methods of Treatment

Provided herein is a method of treating a viral infection, particularly an HIV infection, comprising administering about 2.5 mg to about 20 mg Elvucitabine per day, to a patient suffering from a viral infection.

About 5 mg Elvucitabine is administered twice a day, for example.

About 2.5, about 5 mg, about 7.5 mg, or about 10 mg Elvucitabine is administered once per day in other embodiments.

Also provided herein is method of treating a viral infection, comprising administering about 5 mg to about 20 mg Elvucitabine per 48 hour interval to a patient suffering from a viral infection, for example and HBV or HIV infection.

In certain embodiments about 10 mg, about 15 mg, or about 20 mg Elvucitabine is administered once per 48 hour interval.

A method of treating a viral infection comprising administering about 40 mg to about 100 mg Elvucitabine per week to a patient suffering from a viral infection, is further provided. Typically the viral infection treated will be an HBV or HIV infection. Methods of administering the Elvucitabine as an oral dosage form are preferred.

For example about 40 mg, about 50 mg, about 75 mg, or about 100 mg Elvucitabine is administered once per week. In one embodiment, Elvucitabine is administered once every 2 to 7 days.

In certain embodiments described herein the Elvucitabine is administered as an oral dosage form. Oral dosages of Elvucitabine may be in the form of a tablet or capsule, or other pharmaceutically acceptable form.

Also provided herein are methods of increasing patient compliance with anti-viral therapy, such as treatment of an HIV or HBV infection, by providing reverse transcriptase inhibitor formulated for low dose daily administration. Methods of increasing patient compliance with anti-HIV therapy by providing a reverse transcriptase inhibitor formulated for administration of about 2.5 to about 10 mg of the reverse transcriptase inhibitor daily are included in the invention. A method of increasing patient compliance with anti-viral therapy by providing a reverse transcriptase inhibitor formulated for administration of about 5 to about 20 mg of the reverse transcriptase inhibitor once every 48 hour interval or of about 40 to about 100 mg of the reverse transcriptase inhibitor once every one week interval are also within the scope of the invention.

Elvucitibane is the preferred reverse transcriptase inhibitor used in such formulations. In certain embodiments the anti-viral therapy is treatment of an HBV or HIV infection.

Pharmaceutical Formulations

Provided herein are pharmaceutical formulations for low dosage and/or low frequency administration, comprising Elvucitibine or a salt thereof and at least one carrier or excipient.

The pharmaceutical formulation may be in the form suitable for administration, but is preferably an oral dosage form such as a tablet or capsule.

Dosage Forms Characterized by AUC

Elvucitabine forms for low dosage administration described herein exhibit characteristic plasma concentrations over time. When integrated the graph of plasma concentration over time provides a characteristic "area under the curve" or AUC.

Preferred Elvucitabine dosage forms described herein exhibit an AUC at steady state for a 24 hour period of about 300 microgram hour/liter (μg h/L).

Exemplary Formulations

The low dosage formulations provided herein may be formulated by a variety of methods apparent to those of skill in the art of pharmaceutical formulation. Suitable formulations include, for example, tablets, capsules, press coat formulations, easily administered formulations, etc.

Preparation of Dosage Forms

The term "dosage form" denotes a form of a formulation that contains an amount sufficient to achieve a therapeutic effect with a single administration. Suitable formulations include, for example, tablets, capsules, press coat Formulations, etc.

When the formulation is a tablet or capsule, the dosage form is usually one such tablet or capsule. The frequency of administration that will provide the most effective results in an efficient manner without overdosing will vary with the characteristics of the particular formulation, including both its pharmacological characteristics and its physical characteristics such as solubility, and with the characteristics of the swellable matrix such as its permeability, and the relative amounts of the active agent and polymer. In most cases, the dosage form will be such that effective results will be achieved with administration no more frequently than once every eight hours or more, preferably once every twelve hours or more, and even more preferably once every twenty-four hours or more.

The dosage form can be prepared by various conventional mixing, comminution and fabrication techniques readily apparent to those skilled in the chemistry of drug formulations. Examples of such techniques are as follows:

(1) Direct compression, using appropriate punches and dies; the punches and dies are fitted to a suitable rotary tableting press;
(2) Injection or compression molding using suitable molds fitted to a compression unit
(3) Granulation followed by compression; and
(4) Extrusion in the form of a paste, into a mold or to an extrudate to be cut into lengths.

When particles are made by direct compression, the addition of lubricants may be helpful and sometimes important to promote powder flow and to prevent capping of the particle (breaking off of a portion of the particle) when the pressure is relieved. Useful lubricants are magnesium stearate (in a concentration of from 0.05% to 3% by weight, preferably less than 1% by weight, in the powder mix), and hydro genated vegetable oil (preferably hydrogenated and refined triglycerides of stearic and palmitic acids at about 1% to 5% by weight, most preferably about 2% by weight. Additional excipients may be added to enhance powder flowability and reduce adherence.

Preparation of Elvucitabine Containing Subunits

Elvucitabine and any optional additives may be prepared in many different ways, for example as subunits. Pellets comprising an active agent can be prepared, for example, by a melt pelletization technique. In this technique, the active agent in finely divided form is combined with a binder and other optional inert ingredients, and thereafter the mixture is pelletized, e.g., by mechanically working the mixture in a high shear mixer to form the pellets (e.g., pellets, granules, spheres, beads, etc., collectively referred to herein as "pellets"). Thereafter, the pellets can be sieved in order to obtain pellets of the requisite size. The binder material may also be in particulate form and has a melting point above about 40° C. Suitable binder substances include, for example, hydrogenated castor oil, hydrogenated vegetable oil, other hydrogenated fats, fatty alcohols, fatty acid esters, fatty acid glycerides, and the like, and combinations comprising one or more of the foregoing binders.

Oral dosage forms may be prepared to include an effective amount of melt-extruded subunits containing Elvucitabine in the form of multiparticles within a capsule. For example, a plurality of the melt-extruded multiparticulates can be placed in a gelatin capsule in an amount sufficient to provide an effective release dose when ingested and contacting by gastric fluid.

Subunits, e.g., in the form of multiparticulates, can be compressed into an oral tablet using conventional tableting equipment using standard techniques. The tablet formulation may include excipients such as, for example, an inert diluent such as lactose, granulating and disintegrating agents such as cornstarch, binding agents such as starch, and lubricating agents such as magnesium stearate.

Alternatively, the subunits containing Elvucitabine are added during the extrusion process and the extrudate can be shaped into tablets by methods know in the art. The diameter of the extruder aperture or exit port can also be adjusted to vary the thickness of the extruded strands. Furthermore, the exit part of the extruder need not be round; it can be oblong, rectangular, etc. The exiting strands can be reduced to particles using a hot wire cutter, guillotine, etc.

A melt-extruded multiparticulate system can be, for example, in the form of granules, spheroids, pellets, or the like, depending upon the extruder exit orifice. The terms "melt-extruded multiparticulate(s)" and "melt-extruded multiparticulate system(s)" and "melt-extruded particles" are used interchangeably herein and include a plurality of subunits, preferably within a range of similar size and/or shape. The melt-extruded multiparticulates can be about 0.1 to about 12 mm in length and have a diameter of about 0.1 to about 5 mm. In addition, the melt-extruded multiparticulates can be any geometrical shape within this size range. Alternatively, the extrudate can simply be cut into desired lengths and divided into unit doses of active agent without the need of a spheronization step.

The melt-extruded dosage forms can further include combinations of melt-extruded multiparticulates containing one or more of the therapeutically active agents before being encapsulated.

The oral dosage form containing active agent may be in the form of micro-tablets enclosed inside a capsule, e.g. a gelatin capsule. For this, a gelatin capsule as is employed in pharmaceutical formulations can be used, such as the hard gelatin capsule known as CAPSUGEL, available from Pfizer.

Particles

Some oral dosage forms described herein contain Elvucitabine in the form of particles. Such particles may be compressed into a tablet, present in a core element of a coated dosage form, such as a taste masked dosage form, a press coated dosage form, or an enteric coated dosage form, or may be contained in a capsule, osmotic pump dosage form, or other dosage form.

For particles, such as powder particles, present in the core element of a coated dosage form, the core element may have a particle size distribution with a median of about 100 μm. The particles in the distribution may vary from about 1 μm to about 250 μm, more preferably from 25 μm to about 250 μm, most preferably about 35 μm to about 125 μm. If the median of the distribution is close to either extreme of the distribution, the taste masking or sustained-release characteristics may be affected. In a particle size range of about 25 μm to about 250 μm, no more than about 25% of particles can be less than about 25 μm, and no more than about 25% can be over about 250 μm.

Another parameter to consider is particle shape. Particle shape can influence the coverage and stability of the coat. Both the crystallinity of the active agent and the aspect ratio of the particles are related to particle shape. In certain embodiments it is desirable for the Elvucitabine of the coated dosage forms have crystalline morphology, however, sharp angles on a crystal can cause weaknesses in the coat. These sharp corners may lead to stress points on the coat and cause weaknesses in the structure possibly leading to premature release of active agent from the dosage form. Furthermore, areas of thin coating are susceptible to breaking and cracking and hence ineffective for sustained-release and taste masking.

Regarding the aspect ratio, a low aspect ratio is preferred. The aspect ratio is a measure of the thickness to diameter. For example, a low aspect ratio of about 1 would be a box or sphere. Crystals with a high aspect ratio are more pointed with needle-like crystals. Crystals with a high aspect ratio may result in a relatively thin coat at the crystal needle tips leading to a more rapid release rate of active agent than is preferred. A low aspect ratio spherical shape of the particle is advantageous for both solubility of the coat and high payload of active agent. Therefore, it is most preferable that the aspect ratio is less than about 1, more preferably about 0.5 to about 1, and most preferably approximately about 0.5 to about 0.6 providing a substantially rounded shape.

Inconsistencies in size and shape can lead to inconsistent coating. Where the particles containing active agent are of different size and shape, polymeric coating materials such as ethyl cellulose may deposit differently on each particle. It is therefore preferable for coated dosage forms that substantially all particles of the dosage form have substantially the same size and shape so that the coating process is better controlled and maintained.

Tablets and Capsules

Tablets typically comprise conventional pharmaceutically compatible adjuvants as inert diluents, such as calcium carbonate, sodium carbonate, mannitol, lactose and cellulose; binders such as starch, methylcellulose, microcrystalline cellulose, gelatin, and sucrose; disintegrants such as starch, alginic acid, sodium starch glycolate, and croscarmelose; and lubricants such as magnesium stearate, stearic acid and talc. Buffering agents such as potassium phosphate, potassium citrate, and sodium phosphate may also be present. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules (including time release and sustained release formulations) typically comprise one or more solid diluents disclosed above. The selection of carrier components often depends on secondary considerations like taste, cost, and shelf stability.

Such compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methylcellulose phthalate, ethyl cellulose, Eudragit coatings, waxes and shellac.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Particular embodiments provided herein include capsules or tables comprising from about 2.5 to about 20 mg Elvucitabine for daily administration, preferably about 5 mg to about 10 mg for daily administration, from about 10 mg to about 20 mg for administration once every 48 hour interval, and from about 40 mg to about 100 mg for once weekly administration.

Pharmaceutical formulations for use in tablets may have certain desirable physical properties. For example the invention provides a pharmaceutical formulation of Elvucitabine having a tensile of from about 1400 KPa to 2100 KPa.

Also provided is pharmaceutical formulation of Elvucitabine having a compression range of 150 to 260 Mpa.

The invention also provides an oral dosage form of Elvucitabine having a hardness of about 3 KGF to about 11.5 KGF.

The invention includes an Elvucitabine oral dosage form, for example a tablet, wherein the core has an aspect ratio of 0.50 to 0.55. The invention includes coated Elvucitabine tablets, wherein the tablet has an aspect ratio of from 0.51 to 0.56.

The invention includes coated tablets 2.5 mg Elvucitabine, wherein the tablet has a an aspect ration of from 0.51 to 0.56 and a diameter of 40 mm or less.

Optional Additional Additives for Formulations

Excipients

Excipients are components added to active agent pharmaceutical formulation other than Elvucitabine, and include inert substances used as a diluent or vehicle for active agent. Excipients may be added to facilitate manufacture, enhance stability, control release, enhance product characteristics, enhance bioavailability, enhance patient acceptability, etc. Pharmaceutical excipients include binders, disintegrants, lubricants, glidants, compression aids, colors, sweeteners, preservatives, suspending agents, dispersing agents, film formers, flavors, printing inks, etc. Binders hold the ingredients in the dosage form together. Exemplary binders include, for example, polyvinyl pyrrolidone, hydroxypropyl cellulose, hydroxypropyl methylcellulose, methylcellulose, and hydroxyethyl cellulose, sugars, and combinations comprising one or more of the foregoing binders. Disintegrants expand when wet causing a tablet to break apart. Exemplary disintegrants include water swellable substances, for example, low-substituted hydroxypropyl cellulose, e.g. L-HPC; cross-linked polyvinyl pyrrolidone (PVP-XL), e.g. Kollidon® CL and Polyplasdone® XL; cross-linked sodium carboxymethylcellulose (sodium croscarmellose), e.g. Ac-disol®, Primellose®; sodium starch glycolate, e.g. Primojel®; sodium carboxymethylcellulose, e.g. Nymcel ZSB10®; sodium carboxymethyl starch, e.g. Explotab®; ion-exchange resins, e.g. Dowex® or Amberlite®; microcrystalline cellulose, e.g. Avicel®; starches and pregelatinized starch, e.g. Starch 1500®, Sepistab ST200®; formalin-casein, e.g. PlasVita®, and combinations comprising one or more of the foregoing water swellable substances. Lubricants, for example, aid in the processing of powder materials. Exemplary lubricants include calcium stearate, glycerol behenate, magnesium stearate, mineral oil, polyethylene glycol, sodium stearyl fumarate, stearic acid, talc, vegetable oil, zinc stearate, and combinations comprising one or more of the foregoing lubricants. Glidants include, for example, silicon dioxide.

In certain embodiments described herein the invention includes a pharmaceutical composition comprising Elvucitabine, lactose monohydrate, and anhydrous lactose. The formulation may also include other ingredients such as crospovidone, calcium silicate, and magnesium stearate.

In certain embodiment the lactose monohydrate and anhydrous lactose taken together comprise about 60 percent to about 90 percent of the Elvucitabine formulation by weight.

The invention provides a pharmaceutical formulation wherein less than 2.0%, less than 1.5%, less than 1.0%, or less than 0.5% is magnesium stearate. The invention also provides a pharmaceutical formulation containing Elvucitabine and magnesium stearate, wherein from about 0.05 to about 1 percent, or is some embodiments from about 0.10 to about 0.50 percent, or about 0.05 to about 0.50 percent, of the composition is magnesium stearate.

Fillers

Certain dosage forms described herein contain a filler, such as a water insoluble filler, water soluble filler, and combinations thereof. The filler may be a water insoluble filler, such as silicon dioxide, titanium dioxide, talc, alumina, starch, kaolin, polacrilin potassium, powdered cellulose, microcrystalline cellulose, and combinations comprising one or more of the foregoing fillers. Exemplary water-soluble fillers include water soluble sugars and sugar alcohols, preferably lactose, glucose, fructose, sucrose, mannose, dextrose, galactose, the corresponding sugar alcohols and other sugar alcohols, such as mannitol, sorbitol, xylitol, and combinations comprising one or more of the foregoing fillers.

Coatings

The formulations described herein may be coated with a functional or non-functional coating. The coating may comprise about 0 to about 40 weight percent of the composition. The coating material may include a polymer, preferably a film-forming polymer, for example, methyl cellulose, ethyl cellulose, hydroxypropyl cellulose, hydroxypropyl methyl cellulose, hydroxybutyl methyl cellulose, cellulose acetate, cellulose propionate (lower, medium or higher molecular weight), cellulose acetate propionate, cellulose acetate butyrate, cellulose acetate phthalate, carboxymethyl cellulose, cellulose triacetate, cellulose sulphate sodium salt, poly(methyl methacrylate), poly(ethyl methacrylate), poly(butyl methacrylate), poly(isobutyl methacrylate), poly(hexyl methacrylate), poly(phenyl methacrylate), poly(methyl acrylate), poly(isopropyl acrylate), poly(isobutyl acrylate), poly(octadecyl acrylate), poly(ethylene), poly(ethylene) low density, poly(ethylene) high density, (poly propylene), poly(ethylene glycol poly(ethylene oxide), poly(ethylene terephthalate), poly(vinyl alcohol), poly(vinyl isobutyl ether), poly(vinyl acetate), poly(vinyl chloride), polyvinyl pyrrolidone, and combinations comprising one or more of the foregoing polymers.

The coating may form a moisture barrier, act as sealant, or as an enteric coat. Appropriate coatings for these purposes include Aquacoat® ECD, Opadry® AMB, Sepifilm™ LP, Surelease®. The coating may also be an enteric coating such as Aquacoat® CPD or Acryl-Eze®.

In applications such as taste-masking, the polymer can be a water-insoluble polymer. Water insoluble polymers include ethyl cellulose or dispersions of ethyl cellulose, acrylic and/or methacrylic ester polymers, cellulose acetates, butyrates or propionates or copolymers of acrylates or methacrylates having a low quaternary ammonium content, and the like, and combinations comprising one or more of the foregoing polymers.

In controlled-release applications, for example, the coating can be a hydrophobic polymer that modifies the release properties of active agent from the formulation. Suitable hydrophobic or water insoluble polymers for controlled-release include, for example, methacrylic acid esters, ethyl cellulose, cellulose acetate, polyvinyl alcohol-maleic anhydride copolymers, β-pinene polymers, glyceryl esters of wood resins, and combinations comprising one or more of the foregoing polymers.

The inclusion of an effective amount of a plasticizer in the coating composition may improve the physical properties of the film. For example, because ethyl cellulose has a relatively high glass transition temperature and does not form flexible films under normal coating conditions, it may be advantageous to add plasticizer to the ethyl cellulose before using the same as a coating material. Generally, the amount of plasticizer included in a coating solution is based on the concentration of the polymer, e.g., most often from about 1 to about 50 percent by weight of the polymer. Concentrations of the plasticizer, however, can be determined by routine experimentation.

Examples of plasticizers for ethyl cellulose and other celluloses include plasticizers such as dibutyl sebacate, diethyl phthalate, triethyl citrate, tributyl citrate, triacetin, and combinations comprising one or more of the foregoing plasticizers, although it is possible that other water-insoluble plasticizers (such as acetylated monoglycerides, phthalate esters, castor oil, etc.) can be used.

Examples of plasticizers for acrylic polymers include citric acid esters such as triethyl citrate 21, tributyl citrate, dibutyl phthalate, 1,2-propylene glycol, polyethylene glycols, propylene glycol, diethyl phthalate, castor oil, triacetin, and combinations comprising one or more of the foregoing plasticizers, although it is possible that other plasticizers (such as acetylated monoglycerides, phthalate esters, castor oil, etc.) can be used.

An example of a functional coating comprises a coating agent comprising a poorly water-permeable component (a) such as, an alkyl cellulose, for example an ethylcellulose, such as AQUACOAT (a 30% dispersion available from FMC, Philadelphia, Pa.) or SURELEASE (a 25% dispersion available from Colorcon, West Point, Pa.) and a water-soluble component (b), e.g., an agent that can form channels through the poorly water-permeable component upon the hydration or dissolution of the soluble component. The functional coating may also be an enteric coating, which facilitates drug dissolution in the intestine rather than in the stomach.

The functional coating may comprise about 1% to about 40%, or about 3% to about 30%, or about 5% to about 25%, and or about 8% to about 25% of the total formulation. For pellet formulations it is preferred that the coating comprise from about 1% to about 40%, or from about 5% to about 25%, or from about 10% to about 25% of the total pellet weight. For tablet formulations the coating may comprise from about 5% to about 40%, or from about 8% to about 25%, or about 17.5% of the total formulation.

In certain embodiments, particularly where the coating provides taste masking, it is preferred that the coating is substantially continuous coat and substantially hole-free. By "substantially continuous coating" is meant a coating, which retains a smooth and continuous appearance when magnified 1000 times under a scanning electron microscope and wherein no holes or breakage of the coating are evident.

Suitable methods can be used to apply the coating to active agent. Processes such as simple or complex coacervation, interfacial polymerization, liquid drying, thermal and ionic gelation, spray drying, spray chilling, fluidized bed coating, pan coating, electrostatic deposition, may be used. A substantially continuous nature of the coating may be achieved, for example, by spray drying from a suspension or dispersion of active agent in a solution of the coating composition including a polymer in a solvent in a drying gas having a low dew point.

When a solvent is used to apply the coating, the solvent is preferably an organic solvent that constitutes a good solvent for the coating material, but is substantially a non-solvent or poor solvent for an active agent. While an active agent may partially dissolve in the solvent, it is preferred that the active ingredient will precipitate out of the solvent during the spray drying process more rapidly than the coating material. The solvent may be selected from alcohols such as methanol, ethanol, halogenated hydrocarbons such as dichloromethane (methylene chloride), hydrocarbons such as cyclohexane, and combinations comprising one or more of the foregoing solvents. Dichloromethane (methylene chloride) has been found to be particularly suitable.

The concentration of polymer in the solvent will normally be less than about 75% by weight, and typically about 10 to about 30% by weight. After coating, the coated dosage forms may be allowed to cure for at least about 1 to about 2 hours at a temperature of about 50° C. to about 60° C., more preferably of about 55° C.

The coatings may be about 0.005 micrometers to about 25 micrometers thick, preferably about 0.05 micrometers to about 5 micrometers.

Packaged Formulations

Packaged pharmaceutical formulations comprising an Elvucitabine pharmaceutical formulation and instructions for using the formulation for treating a viral infection, such as an HIV infection, by administering about 2.5 to about 10 mg Elvucitabine per day, or treating a patient having a viral infection by administering about 5 mg to about 20 mg Elvucitabine per 48 hour interval, or about 40 mg to about 100 mg Elvucitabine per week to a patient suffering from a viral infection are further provided herein. Typically the instructions will be instructions for using the formulation to treat an HBV or HIV infection. Packaged formulations in which the Elvuticabine is present as an oral dosage form are disclosed herein.

The invention includes providing prescribing information, for example, to a patient or health care provider, or as a label in a packaged pharmaceutical formulation. Prescribing information may include for example efficacy, dosage and administration, contraindication and adverse reaction information pertaining to the pharmaceutical formulation.

EXAMPLES

The following examples further illustrate the invention but, of course, should not be construed as in any way limiting its scope.

Example 1

Low Dose Elvucitabine Tablets

Elvucitabine exhibits adhesion (to metal surfaces) and limited compatibility Tropical excipients used to resolve such issues in a direct blend are not preferable based on the excipient compatibility results. Excipients that increase compactability, decrease adhesion, and are not acidic are desirable to address processing challenges.

All tablets are compressed using ¼" standard concave tooling.

The following 5 mg dosage form is made at a 150 gram batch size and large enough to run a few rotations on the automated press. The 20 mg dosage form is made at smaller batch sizes (40 grams) to conserve drug, and therefore is not evaluated under full conditions of an automated press. However the tablets made from hand turning of the wheel resulted in tablets with good surfaces, hardness and friability. The 5 mg tablets pass content uniformity specifications (range: 85%-115%; % RSD</=6%) with CU=87.8% and % RSD=1.7.

| Component | % | mg/tablet | g/1000 tablets |
|---|---|---|---|
| Elvucitabine | 3.33 | 5 | 5.0 |
| Lactose (Fast Flo) | 45.21 | 67.815 | 67.815 |
| Lactose (Anhydrous-Direct tableting Grade) | 45.21 | 67.815 | 67.815 |
| Crospovidone | 3 | 4.5 | 4.5 |
| Calcium Silicate | 2 | 3.0 | 3.0 |
| Magnesium Stearate | 1.25 | 1.875 | 1.875 |
| TOTALS | 100% | 150 mg | 150 g |

Hardness: 5.3 Kp, Friability: 0.34%, no capping

| Component | % | mg/tablet | g/200 tablets |
|---|---|---|---|
| Elvucitabine | 10 | 20 | 4.0 |
| Lactose (Fast Flo) | 41.875 | 83.75 | 16.75 |
| Lactose (Anhydrous-Direct tableting Grade) | 41.875 | 83.75 | 16.75 |
| Crospovidone | 3 | 6 | 1.2 |
| Calcium Silicate | 2 | 4 | 0.8 |
| Magnesium Stearate | 1.25 | 2.5 | 0.5 |
| TOTALS | 100% | 200 mg | 40 g |
| Hardness: 5.9 Kp, Friability: 0%, no capping | | | |
| Elvucitabine | 25 | 50 | 10 |
| Lactose (Fast Flo) | 34.375 | 68.75 | 13.75 |
| Lactose (Anhydrous-Direct tableting Grade) | 34.375 | 68.75 | 13.75 |
| Crospovidone | 3 | 6 | 1.2 |
| Calcium Silicate | 2 | 4 | 0.8 |
| Magnesium Stearate | 1.25 | 2.5 | 0.5 |
| TOTALS | 100% | 200 mg | 40 g |

Hardness: 4.5 Kp, Friability: 0%, no capping

Two additional batches are made for the 5 mg and 20 mg dose with an additional blending step. Content uniformity results are also presented below. The extra blending step results in a more optimum content uniformity. The 5 mg and 20 mg dose are formulated to a total tablet weight of 150 mg and the 50 mg dose is tableted to a total tablet weight of 200 mg.

| | 5 mg dose | | 20 mg dose | |
|---|---|---|---|---|
| Component | % | mg/tablet | % | mg/tablet |
| Elvucitabine | 3.33 | 5.0 | 13.33 | 20.00 |
| Lactose (Fast Flo) | 45.21 | 67.81 | 40.21 | 60.32 |
| Lactose (Anhydrous-Direct tableting Grade) | 45.21 | 67.81 | 40.21 | 60.32 |
| Crospovidone | 3.00 | 4.50 | 3.00 | 4.50 |
| Calcium Silicate | 2.00 | 3.00 | 2.00 | 3.00 |
| Magnesium Stearate | 1.25 | 1.88 | 1.25 | 1.87 |
| TOTALS | 100 | 150 | 100 | 150 |

Content Uniformity Data

| | % CU | % RSD |
|---|---|---|
| 5 mg dose | 89.4 | 4.6 |
| 20 mg dose | 93.2 | 4.4 |

Example 2

Coated Tablets

Coated tablets are prepared with the application of a "base-coat" of hydroxypropylmethylcellulose (OpaDry). This coating agent smoothes tablet surface imperfections, providing a suitable surface for adhesion of the enteric coat.

| | |
|---|---|
| Core | Elvucitabine (20 mg) Tablets |
| Load | 100 tabs     15.033 g |
| Coating System | Sureteric (15% dispersion) |
| Target Coating Level | 14% |
| Coated Product | (20 mg) Enteric Coated Tablets (Sureteric) |

Coated tablets appear to have a uniform, slightly rough, off-white coat. Six tablets tested in 0.1 N HCl—all passed.

| | |
|---|---|
| Core | Elvucitabine (20 mg) Tablets |
| Load | 100 tabs     15.031 g |
| Coating System | Eudragit L30 D55 with 10% Triethylcitrate |
| Target Coating Level | 14% |
| Coated Product | (20 mg) Enteric Coated Tablets (Eudragit) |

Acceptable tablets obtained—slightly rough surface with glossy finish.

Six tablets tested in 0.1 N HCl—all passed.

| | |
|---|---|
| Core | Elvucitabine (20 mg) Tablets |
| Load | 100 tabs     15.01 g |
| Coating System | Opadry followed by Eudragit L30 D55 with 2% TEC |
| Target Coating Level | 14%   (2% Opadry/12% Eudragit) |
| Coated Product | ACH 126,443 (20 mg) Enteric Coated Tablets (Opadry/Eudragit) |

15% dispersion of Opadry Clear (YS-1-7472)

Opadry coat=excellent, glossy surface.

Example 3

Additional Coated Tablets

The following formulations are prepared by blending the first five ingredients, Elvucitabine, lactose fast flow, lactose anhydrous, crospovidone, and calcium silicate for 13 minutes. Magnesium stearate is then added. Formulations having more that 0.5 percent magnesium stearate by weight are blended approximately 3 minutes longer. Formulations containing about 0.5% magnesium stearate or less are blended and additional 20-25 minutes. Tabletting is performed as described in Example 1 and the enteric and final coat are applied.

| | mg/tablet | % | mg/tablet | % |
|---|---|---|---|---|
| Ingredient | | | | |
| 2.5 mg Strength | | | | |
| Elvucitabine | 2.5 | 3.33 | 2.5 | 3.33 |
| Lactose fast flow | 36.626 | 44.835 | 34.406 | 45.785 |

| -continued | | | | |
|---|---|---|---|---|
| Lactose Anhydrous | 36.626 | 44.835 | 34.406 | 45.785 |
| Crospovidone | 4.5 | 3.00 | 4.5 | 3.00 |
| Calcium Silicate | 3.0 | 2.00 | 3.0 | 2.00 |
| Magnesium Stearate | 3.0 | 2.00 | 0.15 | 0.10 |
| Total Ingredient | 75.0 | 100.0 | 75.0 | 150.0 |
| 5 mg Strength | | | | |
| Elvucitabine | 5.0 | 3.33 | 5.0 | 3.33 |
| Lactose fast flow | 67.25 | 44.835 | 68.678 | 45.785 |
| Lactose Anhydrose | 67.25 | 44.835 | 68.678 | 45.785 |
| Crospovidone | 4.5 | 3.00 | 4.5 | 3.00 |
| Calcium Silicate | 3.0 | 2.00 | 3.0 | 2.00 |
| Magnesium Stearate | 3.0 | 2.00 | 0.15 | 0.10 |
| Total Ingredient | 150.0 | 100.0 | 150.0 | 150.0 |
| 20 mg Strength | | | | |
| Elvucitabine | 20.0 | 13.33 | 20.0 | 13.33 |
| Lactose fast flow | 59.75 | 39.83 | 61.095 | 40.73 |
| Lactose Anhydrose | 59.75 | 39.83 | 61.095 | 40.73 |
| Crospovidone | 4.5 | 3.00 | 4.5 | 3.00 |
| Calcium Silicate | 3.0 | 2.00 | 3.0 | 2.00 |
| Magnesium Stearate | 3.0 | 2.00 | 0.30 | 0.20 |
| Total Ingredient | 150 | 100 | 150 | 100 |
| 50 mg Strength | | | | |
| Elvucitabine | 50.0 | 25.0 | 50.0 | 25.0 |
| Lactose fast flow | 68.0 | 34.0 | 69.85 | 34.925 |
| Lactose Anhydrose | 68.0 | 34.0 | 69.85 | 34.925 |
| Crospovidone | 6.0 | 3.00 | 3.00 | 3.00 |
| Calcium Silicate | 4.0 | 2.00 | 2.00 | 2.00 |
| Magnesium Stearate | 4.0 | 2.00 | 0.225 | 0.15 |
| Total | 150 | 100 | 150 | 100 |
| 5 mg Strength | | | | |
| Elvucitabine | 5.0 | 3.33 | | |
| Lactose fast flow | 68.37 | 45.58 | | |
| Lactose Anhydrose | 68.37 | 45.58 | | |
| Crospovidone | 4.5 | 3.00 | | |
| Calcium Silicate | 3.0 | 2.00 | | |
| Magnesium Stearate | 0.75 | 0.50 | | |

| Tablet Coating System | | Dispersion Concentration | % Tablet weight gain |
|---|---|---|---|
| Base coat | Opadry II | 15% | 2 |
| Enteric coat | Eudragit L30 D55/TEC | 28.5%/5% | 12 |

What is claimed is:

1. A method of treating a retrovirus infection comprising administering about 5 mg to about 20 mg Elvucitabine once per 48 hour interval or about 40 to 100 mg optically active Elvuctiabine once per one week interval to a human patient suffering from a retrovirus infection.

2. The method of claim 1 wherein about 10 mg Elvucitabine is administered once per 48 hour interval.

3. The method of claim 1 wherein about 15 mg Elvucitabine is administered once per 48 hour interval.

4. The method of claim 1 wherein about 20 mg Elvucitabine is administered once per 48 hour interval.

5. The method of claim 1 wherein about 40 mg optically active Elvucitabine is administered once per week.

6. The method of claim 1 wherein about 50 mg optically active Elvucitabine is administered once per week.

7. The method of claim 1 wherein about 75 mg optically active Elvucitabine is administered once per week.

8. The method of claim 1 wherein about 100 mg optically active Elvucitabine is administered once per week.

9. The method of claim 1 wherein the viral infection is a HBV or HIV infection.

10. The method of claim 1 wherein the optically active Elvucitabine is administered as an oral dosage.

11. The method of claim 10 wherein the oral dosage is in the form of a tablet or capsule.

* * * * *